(12) United States Patent
Moa et al.

(10) Patent No.: US 9,016,275 B2
(45) Date of Patent: Apr. 28, 2015

(54) NEBULISING DEVICE FOR USE IN A CPAP-SYSTEM

(75) Inventors: Gunnar Moa, Gothenburg (SE); Kjell Nilsson, Östersund (SE)

(73) Assignee: Neores AB (SE)

( * ) Notice: Subject to any disclaimer, the term of this patent is extended or adjusted under 35 U.S.C. 154(b) by 526 days.

(21) Appl. No.: 12/746,901

(22) PCT Filed: Dec. 19, 2008

(86) PCT No.: PCT/SE2008/051519
§ 371 (c)(1),
(2), (4) Date: Sep. 14, 2010

(87) PCT Pub. No.: WO2009/078805
PCT Pub. Date: Jun. 25, 2009

(65) Prior Publication Data
US 2011/0000487 A1    Jan. 6, 2011

Related U.S. Application Data

(60) Provisional application No. 61/014,765, filed on Dec. 19, 2007.

(30) Foreign Application Priority Data

Dec. 19, 2007 (SE) ...................................... 0702842

(51) Int. Cl.
*A61M 15/00* (2006.01)
*A61M 11/00* (2006.01)
(Continued)

(52) U.S. Cl.
CPC ....... *A61M 16/0666* (2013.01); *A61M 16/0858* (2014.02); *A61M 11/00* (2013.01); *A61M 16/14* (2013.01); *A61M 2202/0208* (2013.01)

(58) Field of Classification Search
USPC .............. 128/203.12–203.14, 204.28, 204.21
See application file for complete search history.

(56) References Cited

U.S. PATENT DOCUMENTS 5,193,532 A * 3/1993 Moa et al. ................ 128/204.25
6,814,075 B2   11/2004 Boussignac
(Continued)

FOREIGN PATENT DOCUMENTS

CN    1494446 A    5/2004
EP    0447443 B1   10/1993
(Continued)

OTHER PUBLICATIONS

"International Application Serial No. PCT/SE2008/051519, International Preliminary Report on Patentability dated Oct. 7, 2009", 8 pgs.
(Continued)

*Primary Examiner* — Rachel Young
(74) *Attorney, Agent, or Firm* — Schwegman Lundberg & Woessner, P.A.

(57) ABSTRACT

The present invention relates to a modified nebulizing device for generating a nasal continuous positive airway pressure (CPAP) and addition of nebulized drug which can be carried out simultaneously and in synergy without loosing a substantial amount of nebulized drug. Further, the present invention also discloses a nebulizing device and a nebulizing attachment device usable in a system for generating continuous positive airway pressure (CPAP) and simultaneously and in synergy adding of nebulized drug without loosing a substantial amount of nebulized drug.

6 Claims, 3 Drawing Sheets

(51) Int. Cl.
*A61M 16/06* (2006.01)
*A61M 16/08* (2006.01)
*A61M 16/14* (2006.01)

(56) References Cited

U.S. PATENT DOCUMENTS

| | | | |
|---|---|---|---|
| 7,047,968 B2 | 5/2006 | Kniewasser | |
| 7,600,511 B2* | 10/2009 | Power et al. | 128/200.24 |
| 2002/0020412 A1* | 2/2002 | Gilbert et al. | 128/203.12 |
| 2004/0154617 A1* | 8/2004 | Enk | 128/203.12 |
| 2005/0229927 A1* | 10/2005 | Fink et al. | 128/203.12 |
| 2005/0229928 A1* | 10/2005 | Ivri et al. | 128/203.12 |
| 2007/0049841 A1 | 3/2007 | Lepel | |
| 2009/0000615 A1* | 1/2009 | Pohlmann et al. | 128/200.21 |
| 2010/0286031 A1* | 11/2010 | Charan et al. | 514/3.1 |

FOREIGN PATENT DOCUMENTS

| | | |
|---|---|---|
| WO | WO-2007/024812 A1 | 3/2007 |
| WO | WO-2007/030162 A2 | 3/2007 |
| WO | WO-2009/078805 A1 | 6/2009 |

OTHER PUBLICATIONS

"International Application Serial No. PCT/SE2008/051519, International Search Report mailed May 13, 2009", 7 pgs.

"International Application Serial No. PCT/SE2008/051519, Written Opinion mailed Oct. 20, 2009", 7 pgs.

\* cited by examiner

NEBULISING DEVICE FOR USE IN A CPAP-SYSTEM

RELATED APPLICATIONS

This application is a U.S. National Stage Filing under 35 U.S.C. 371 from International Patent Application Serial No. PCT/SE2008/051519, filed Dec 19, 2008, and published on Jun. 25, 2009 as WO 2009/078805 A1, which claims the priority benefit of U.S. Provisional Application Ser. No. 61/014,765, filed Dec. 19, 2007, and Sweden Application No. 0702842-6, filed Dec. 19, 2007, the contents of which applications and publication are incorporated herein by reference in their entirety.

BACKGROUND OF THE INVENTION

The present invention relates to a modified nebulizing device for generating a nasal continuous positive airway pressure (CPAP) and addition of nebulized drug which can be carried out simultaneously and in synergy without loosing a substantial amount of nebulized drug. Further, the present invention also discloses a nebulizing device and a modified nebulizing CPAP device usable in a system for generating a continuous positive airway pressure (CPAP) and simultaneously and in synergy adding of nebulized drug without loosing a substantial amount of nebulized drug.

There exists devices for generating a continuous positive airway pressure. Such a device is disclosed in EP-B1-0447 443.

It is known that in respiratory treatment of neonates additional treatment with drug is often required. Today use of ancillary masks with upstream drug atomizers are known but then the respiratory treatment of neonates has to be interrupted. U.S. Pat. No. 7,047,968 discloses a nasal CPAP device wherein the drug flow is introduced via a second opening directed into a hollow body and via a first opening is the respiratory gas flow introduced. However, a problem when introducing the drug in this way is that air stream that generates the pressure blows against the hole in the small hollow body and a part of this air stream washes out the hollow body and takes part of the nebulized drug out through the pressure generating hole and also causes a dilution of the drug which is being introduced into the hollow body. U.S. Pat. No. 7,047,968 introduces a nasal CPAP device in such a way that respiratory treatment of neonates does not have to be interrupted to provide additional treatment with drug. Experiments has been carried out using a device as disclosed in EP-B1-0447 443 wherein the drug flow is introduced via the inlet channel for fresh gas. This results in the similar problem as above. Another problem is that the drug particles introduced as disclosed above falls out as liquid and do not remains aerosolized during the transport in the tube and thus never reaches the subjects airway or lungs.

If nebulized drug is introduced via the expiratory channel most of the nebulized drug is lost almost instantly. Further, if the pressure gauge measuring tube is replaced with a wider tube enough amount of nebulized drug is introduced but the main part of said nebulized drug would be lost through the expiratory channel. The reason for this is that nebulized drug is introduced in the part where pressure generation is taking place and where it is severe turbulence. During most of subjects respiratory cycle is it also at this point a greater inflow than the subjects respiratory volumes and the flow is thus mostly directed away from the child which will blow the nebulized drug away.

Therefore there is a need within the technical field of CPAP and administrating nebulized drug to solve the problem that most of the introduced nebulized drug does not reach the subjects airway, lungs or pulmonary alveolus.

SUMMARY OF THE INVENTION

The purpose of the present invention is therefore to provide a device of the type under consideration which, while retaining its simplicity, makes it possible to sustain a positive airway pressure with minimal pressure variations and addition of nebulized drug can be carried out simultaneously and in synergy without loosing a substantial amount of nebulized drug, i.e. the introduced nebulized drug does not reach the subjects airway, lungs or pulmonary alveolus.

The foregoing problem is solved by devices according to the invention. The inventors have surprisingly in spite of the prior art teaching constructed a device that solves the problems above. The device have several advantages. One is of course the effect that respiratory treatment with CPAP combined with medication, i.e. nebulizing drugs can be carried out simultaneously. Further advantages of the invention is that the device improves the control of the amount of added drug. Yet further advantages is that no large losses/dilution of the drug is taken place. The pressure stability in the CPAP-system is also improved. The ability to control the amount as well as reducing losses/dilution of the drug is especially important when applying expensive drugs.

Therefore, it is an object of the present invention to provide a device that due to the new way of introducing nebulized drug achieves synergistic effects such as solving the problems related to the great loss and dilution of nebulized drug and at the same time improves the pressure stability in the CPAP-system during the time the nebulized drug is introduced. Further, the drug particles introduced via the new nebulizing channel in the device does not fall out as liquid and remains floating during the transport in the channel/tube and thus reaches the subjects airway or lungs. The nebulized drug particles size should remains typically about 3-5µ i.e. floating until they reach the lungs where they falls out. The used nebulizer could also effect the nebulized drug particles size as well as the shape of used supply channels.

The inventors have solved the problems by introducing a nebulizing channel positioned in a specific position and in relation to a specific geometric construction, i.e. a specific angle.

The new nebulizing devices will use part of the pneumatic principles that are effective in the CPAP-system. The geometric shape and also the relation between the different channels in the CPAP-system could effect the devices effect.

Other objects and advantages of the present invention will become apparent from the following description and examples.

DEFINITIONS

For purposes of this invention, the term "subject" is intended to encompass a subject in need of nasal continuous positive airway pressure and simultaneously administration of nebulized drug, typically the subject is a child, newborn infant, or similar subjects.

The angle α is intended to be defined as follows. The nebulising channel (34) is positioned at the at least one branch-channel (11) so that the nebulising channel (34) and branch-channel (35) defines an angle α≥120°. The angle can not be above 180°. Further, the angle α is intended to be directed against the subject.

In the application is meant at least one channel or tube even if it is not expressively said so everywhere, i.e. branch-channel 11 should be interpret as at least one branch-channel 11 or a tube 24 should be interpret as at least one tube 24

DETAILED DESCRIPTION OF THE INVENTION

Figure 1:
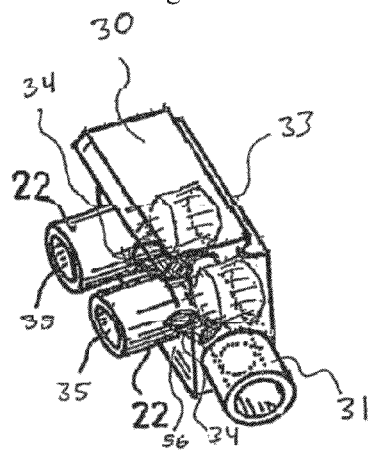
FIG. 1 is a schematic picture in perspective of the nebulising device 30.

As a typical example of the present invention, the present invention is illustrated by a nebulizing device 30 usable in a system for generating a continuous positive airway pressure (CPAP) and simultaneously for adding of nebulized drug, comprising at least one branch-channel 35 which at its one end 33 is adaptable to fit with at least one branch-channel 11 of a CPAP device 19A and which at the other end 36 is adaptable to fit with at least one tube 24 of an attachment device 23 wherein the nebulizing device 30 comprises at least one nebulising channel 34 provided for introducing the nebulized drug, characterized in that the at least one nebulising channel 34 is positioned at the at least one branch-channel 11 so that the at least one nebulising channel (34) and the at least one branch-channel 35 defines an angle $\alpha \geq 120°$.

In a further typical example, the present invention is illustrated by a modified nebulizing device 39 for generating a continuous positive airway pressure (CPAP) and for simultaneously adding of nebulized drug, comprising at least one branch-channel 11 which said at least branch channel 11 is adaptable to fit with at least one tube 24 of an attachment device 23 wherein the modified nebulizing device 39 comprises at least one nebulising channel 34 provided for introducing the nebulized drug, characterized in that the at least one nebulising channel 34 is positioned at the at least one branch-channel 11 so that the at least one nebulising channel 34 and the at least one branch-channel 35 defines an angle $\alpha \geq 120°$.

In a yet further typical example, the present invention is illustrated by a modified nebulizing attachment device 42 usable in a system for generating a continuous positive airway pressure (CPAP) and for simultaneously adding of nebulized drug, wherein the nebulizing attachment device 42 comprises at least one tube 24 and at least one branch-channel 35 connected to each other, wherein the nebulizing attachment device 42 comprises at least one nebulising channel 34 positioned at the at least one branch-channel 35 so that the at least one nebulising channel 34 and the at least one branch-channel 35 defines an angle $\alpha \geq 120°$.

In the devices in the application is the nebulizing channel 34 dimensioned so that the flow speed in the nebulizing channel 34 is essentially lower than the flow speed at the inlet channel 13. Further comments, flow can be 5 l/min in both channels however depending on the dimension of the inlet channel the flow speed can be very different with higher flow speed in a smaller channel than in a larger.

In the devices in the application the nebulising flow in the nebulising channel (34) is between 5-12 l/min.

The devices in the application can be used as a method of treatment for Idiopathic Respiratory Distress syndrome IRDS, Respiratory Distress syndrome RDS, Pneumonia, Obstructive airway disease or similar.

The device according to the invention thus forms in several examples a compact unit in which the air columns in the branch-channels are relatively short in order to avoid backlogs in the gas supply when the pressure tends to fall in the first branch-channel during the inspiration phase.

The compact device made possible according to the invention can be manufactured in plastic in a simple and inexpensive way in several examples. Since it is light in weight, it will not bother the subject when it is secured to his nose or mouth. The unit does not require any moving parts. Depending on the example or other requirements the device can be manufactured in plastic or silicone or other suitable material.

The only tubing that could be necessary is a relatively slender hose for supplying fresh-gas to the fresh-gas inlet channel and tubing connecting the (external) nebulizer to the nebulizing channel 34 direct or to a channel 31 which is connected one or more nebulizing channels 34.

Different examples of the invention disclosed in the application may be combined in any suitable manner to solve foregoing mentioned problems.

FIG. 1 is a schematic picture in perspective of the device 30. FIG. 1 shows the slight extension of the branch-channels 35 which are adaptable to fit a CPAP device channels and nasal attachment tubes. A channel 31 for introducing the nebulized drug is divided or transformed to a nebulising channel 34 at an angle $\alpha$ between branch-channel 35 and nebulising channel 34.

The angle $\alpha$ between the branch channels 35 and nebulizing channel 34 should be $\geq 120°$. In other example the angle $\alpha$ between the channels 35 and 34 should be between 120° and 180°.

Figure 7:
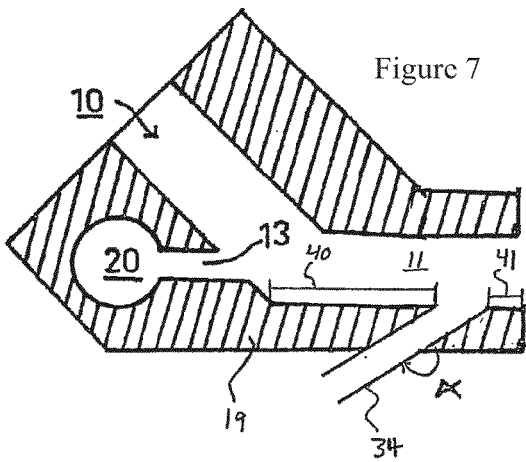
FIG. 7 is an enlarged schematic sectional view through a body of plastic material, in which the required nebulising channel 34 for introducing the nebulized drug is provided at the angle $\alpha$.

Branch-channel 11 is relatively short in length, i.e. the distance 41 in front of the nebulizing channel 34 facing the subject in FIG. 7, preferably five times their diameter at the most. Depending on the example or other requirements the nebulising channel 34 can be manufactured in plastic or silicone or other suitable material.

In another example of the invention, not shown in a Figure, it would be possible to introduce the nebulized drug directly via a nebulising channel 34 at an angle $\alpha$ between the branch channel 35 and the nebulising channel 34, i.e. without using channel 31.

Figure 2:
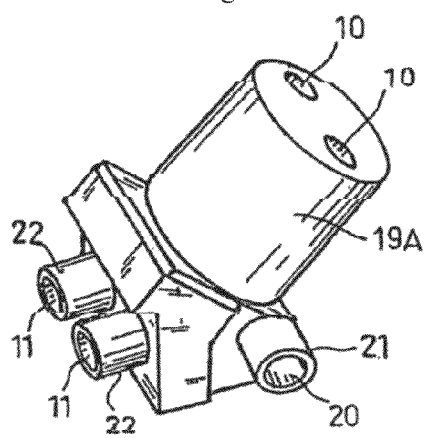
FIG. 2 is a schematic picture in perspective to a CPAP device intended especially if the subject is newborn infants.

FIG. 2 showing the plastic body of a CPAP-device 19A has two parallel systems of branch channels 11. Channel 20 has a connection tube 21 for attachment of a hose for fresh-gas supply.

Figure 3:
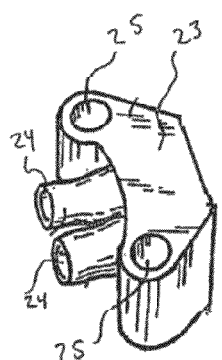
FIG. 3 is a schematic picture in perspective of an attachment device 23 with at least one nasal attachment tube.

FIG. 3 shows the attachment device 23 which has two small prong-like tubes 24 of elastic material. Typical material is silicone. These tubes can be placed in the subjects nose. In turn, these tubes can be attached to tubes 22 in order to fasten the attachment device 23 to the nebulizing device 30. The attachment has two holes 25 for a strip, band or ribbon to be used for holding the attachment in place.

Figure 4:
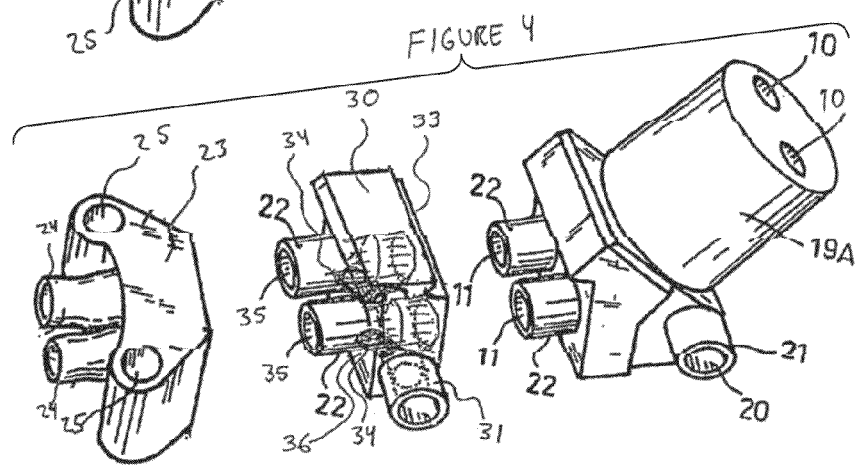
FIG. 4 is a schematic picture in perspective of the nebulizing device 30 adaptable to fit an attachment device 23 and a CPAP device 19A.

FIG. 4 shows the nebulizing device 30 as adaptable to fit the attachment device 23 and the CPAP device 19A. At least one branch channel 35, end 36, is adaptable to fit at least one tube 22 and at least one branch channel 35, end 33, is adaptable to fit at least one branch channel 11. I.e. the nebulizing device 30 can be connected to the attachment device 23 and/or connected to the CPAP device 19A.

This CPAP device is only an example of such and the nebulizing device 30 according to the present invention can fastened to any similar CPAP-device. The nebulizing device 30 is adaptable to fit any similar CPAP-devices and forming a CPAP-system.

Figure 5:
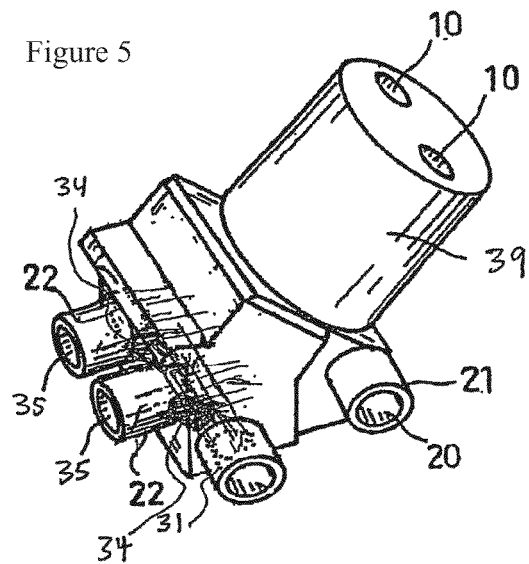
FIG. 5 is a schematic picture in perspective of an example disclosing a modified nebulizing CPAP device 39.

The example disclosed in FIG. 5 is a modified nebulizing CPAP device 39. The modified nebulizing CPAP device 39 with at least one branch-channel 11 to which at least one nebulising channel 34 at an angle α between the at least one branch-channel 11 and at least one nebulising channel 34 and also channel 31 connecting to the at least one nebulising channel 34 for introducing the nebulized drug.

In principle the modified nebulizing CPAP device 39 comprises the nebulizing device 30 incorporated with a CPAP-device 19A forming a modified nebulizing CPAP-system. Which combination in it self could be regarded as an additional example of the invention, see FIG. 5.

In another example of the invention the modified nebulizing device 39 is used for generating by means of ejector action a continuous positive airway pressure (CPAP) and for simultaneously adding of nebulized drug, comprising at least one branch-channel 11 which said at least branch channel 11 is adaptable to fit with at least one tube 24 of an attachment device 23 wherein the modified nebulizing device 39 comprises at least one nebulising channel 34 provided for introducing the nebulized drug, characterized in that the at least one nebulising channel 34 is positioned at the at least one branch-channel 11 so that the at least one nebulising channel 34 and the at least one branch-channel 35 defines an angle α≥120°.

Figure 6:
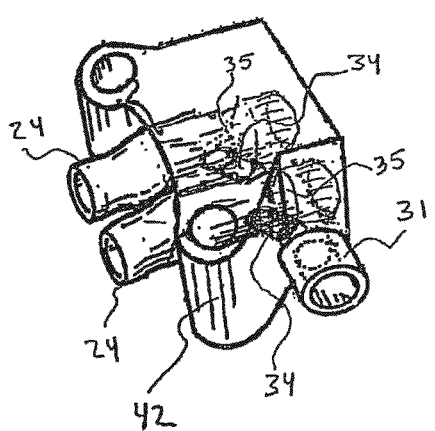
FIG. 6 is a schematic picture in perspective of an example disclosing a modified nebulizing attachment device 42.

FIG. 6 shows another example a modified nebulizing attachment device 42. The end of the at least one tube 24 can be placed in the subjects nose. The other at least one end can be adaptable to a CPAP-device. The modified nebulizing attachment device 42 has two holes 25 for a strip, band or ribbon to be used for holding the modified attachment device 42 in place.

Further, in one example the nebulizing attachment device 42 is usable in a system for adding of nebulized drug without loosing a substantial amount of nebulized drug without adaptable to any CPAP-device, i.e. it is only attached to a nebulizing device or system.

In principle the modified nebulizing attachment device 42 comprises the nebulizing device 30 incorporated with the attachment device 23. Which combination in it self could be regarded as an additional example of the invention, see FIG. 6

FIG. 7 is a sectional view of a body of plastic material 19, in which the channels 11 and 13 in question are provided. Further, the at least one nebulising channel 34 for providing the nebulized drug is positioned at the at least one branch-channel 11 so that the at least one nebulising channel 34 and at least one branch-channel 11 defines an angle α≥120°. Further, disclosed is the supply channel 20 for the supply of fresh gas. Usually two systems of channels 11 and 13 are situated next to each other in the plastic body, and channels 11 can each be attached to a nostril, especially in the case of newborn infants.

Figure 8:
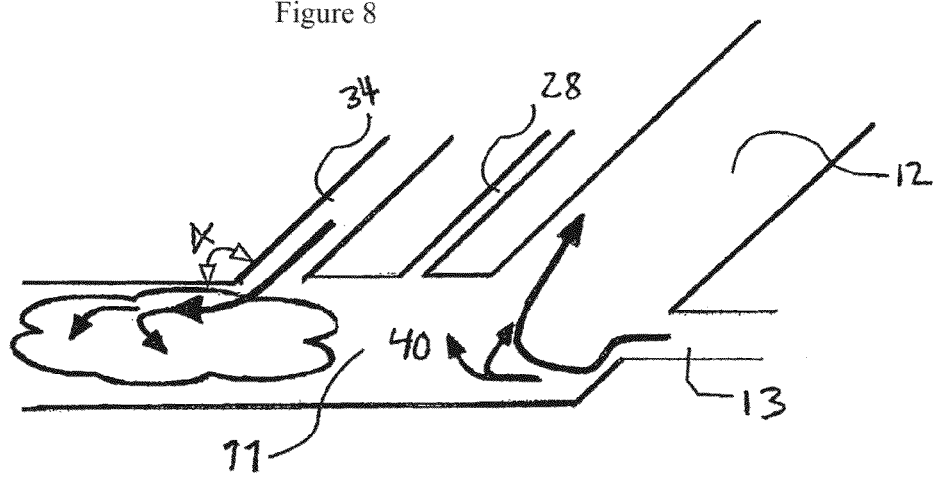
FIG. 8 is a sectional view with stream arrows indicating the for the nebulized drug distribution in an example wherein the device 30 is incorporated into a CPAP device 19A.

FIG. 8 is a schematic sectional view of a similar example as discussed in FIG. 4. The nebulising channel 34 for providing the nebulized drug is positioned at the branch-channel 11 so that the nebulising channel 34 and the branch-channel 11 defines an angle α≥120°. The channel 28 is a separate channel used for measuring the CPAP-pressure which is generated by the flow in the inlet channel 13. There is no gas flow in supply channel 28 and is not disclosed in any other Figures. If such a channel 28 is used the nebulizing channel should be positioned on the side closest to the subject. The circled part shows how the nebulized drug is distributed with arrows and a cloud in the far end of the at least one branch-channel 11 thus without loosing a substantial amount of nebulized drug.

The distance 40 shown in the branch-channel 11 in FIG. 7 can not be too short, it depends of the flow in the inlet channel 13. The distance 41 should be as short as possible, i.e. the nebulizing channel should be positioned as close as possible to the subjects airway.

In one test an attachment device 23 for newborn infants, the channels in the CPAP-system 19A had the following inner diameters. Channel 11 had a diameter of 3.5 mm and channel 13 had a diameter of 1.3 mm. Body 19 is consequently relatively small and light so that it can rest comfortably against the subjects face. Channel 11 is relatively short in length, preferably five times the diameter at the most.

The new nebulising channel 34 should be positioned as close to the subject as possible with out a particular extension of the system. It is important to have a low respiratory flow resistance in a system used for treating a subject who experiences respiratory problems and thus it is not possible to extend the system.

However, if the combination of positioning the new nebulising channel 34 as close as possible to the subject and also make sure that the geometric construction combined with a proper adjusted flow of the carrier gas from the nebulizator carrying the drug it is possible to position the drug containing gas volume as close as possible to the subject and in the closest part of the subjects airway in the nose without extending the system and thereby lowering the capacity of the CPAP-system characteristic features. Important features contributing to the above are:

Dimension, i.e. the diameter of the nebulising channel 34 in proportion to the diameter of the branch-channel 11 or 35.

Carrier gas flow in the nebulising channel 34

Angle α for the nebulising channel 34 in the branch-channel 11 or 35.

The shape of the nebulizing channel 34 can be round, circle, ellipse, rhomb, or other geometrical shape suitable for the application.

The shape of the nebulizing channel 34 entrance in the branch-channel 11 or 35 depends on the shape of the nebulizing channel 34.

The device may typically have the following dimensions in which the at least one branch-channel (11) or (35) has a diameter of 2-5 mm, preferably 2-5 mm and the inlet channel (13) for fresh gas has a diameter of 0.5-2.0 mm, preferably 1-1.3 mm and the flow is between 4-20 l/min, preferably between 4-12 l/min. These features typically applies for all devices disclosed herein.

In one test the device comprised a branch-channel 11 or 35 having a diameter of 3.5 mm. The inlet channel 13 for fresh gas had a diameter of 1.0 mm. The flow here was high, typically between 4-12 l/min.

The nebulizing channel 34 should be dimensioned so that the flow speed is essentially lower than at the inlet channel 13. This is in order for the pressure generated at the nebulizing channel 34 entrance in to the branch-channel 11 or 35 should be as low as possible and always under the pressure that is generated by the inlet channel 13. In this way the pressure generation/regulation in the system is uninterrupted by the nebulising flow. The nebulising flow in the nebulizing channel 34 is typically between 5-12 l/min. Mainly two things effects the nebulizing flow:

Most of the air-driven nebulizators used today generates a flow in that size. But also since the result shows that the maximum breathing speed at an infant during inspiration/inhalation can be as large as 6 l/min. In spite of a breathing volume of 15-30 ml but with a breathing frequency of 40-80 breath/min.

Since the inflow of the nebulising channel 34 is in the same size as the maximum flow during the inspiration/inhalation the main part of the breathed gas will be what is provided from the nebulizator and the fresh gas provided by inlet channel 13 mainly work as pressure regulator during nebulisation and does not dilute the drug in the nebulising channel 34.

During periods when the nebulizator is closed, the flow in the nebulising channel 34 is zero the CPAP-system will work as usual and the fresh gas provided by inlet channel 13 will both be a pressure regulator and supply the subject with the gas mix to be breathed.

In order not to change the subjects oxygen/air mixture when nebulising is taken place should the nebulizator be run with the same mixture as is provided in inlet channel 13. The easy way is to supply the nebulizator with the fresh gas from the same mixer which provide the CPAP-system through the inlet channel 13.

The reason that the angle is flat i.e. above 120° is that the flow should turn and follow the side in the branch-channel 11 or 35, see FIG. 8. This is coursed by the Coanda-effect and the result is that the flow from the nebulising channel 34 will reach yet a further part in toward the subject and when the pressure in the airway changes to the pressure level decided by the inlet channel 13 the flow from the nebulising channel 34 will go out via the branch-channel 11 or 35 and the breathing-channel 10. In this way one has accomplished a gas mixture which has a drug content in the whole part close to the subject part of the CPAP-system and also in a part of the subjects airway in the nose. When then the subject inhales the first part of the breath will (as always reach down to the pulmonary alveolus), completely be the gas mixture from the nebulising channel 34 which means that a good control of the amount/concentration of drug administrated can be achieved. During the rest of the breath due to the flow in the nebulising channel 34 be ≥the maximal inhalation flow, the inhaled drug amount/concentration will be very close to the one which was delivered from the nebulising channel 34. Some dilution will take place from the inlet channel 13 at certain flow conditions depending on that the position of point 40 (the pressure generating turbulent part) in the branch-channel 11, see FIG. 8, is dependent on the breath volume/flow speed.

To illustrate the broad application area several different examples are discussed above.

The CPAP device (19A) as disclosed in EP-B1-0447 443 has been used in the different examples. The CPAP device (19A) is disclosed as follows in one example in EP-B1-0447 443:

A device for generating by means of ejector action a continuous positive airway pressure (CPAP) comprising a breathing-channel (10) which at its one end opens into the atmosphere and at its other end is adapted to be provided with an attachment device (23) to the nose and/or mouth of the patient, and an inlet channel (13) which is connected with the breathing-channel (10) at a point between its ends for fresh gas, the flow of which may be adjusted to obtain an adjustable positive pressure within the breathing-channel, characterized in that the breathing channel (10) comprises a first branch-channel (11) which is connectable to the attachment device and a second branch-channel (12) which opens into the atmosphere, that the two branch-channels together form an angle (A) with each other, that the inlet channel (13) is situated substantially in the extension of the first branch-channel (11) and is connected to the second branch-channel (12) in such a manner that the stream of fresh gas is directed mainly co-axially into the first branch-channel, producing an ejector action, that the cross-sectional area of the respective branch-channel is several times greater than the smallest cross-sectional area of the inlet channel, that the length of each of the branch-channels is relatively short, preferably maximum five times its inner diameter, and that the breathing-channel is built together with the inlet channel to form a compact unit (19, 19A), which can be mounted to the nose and/or mouth of the patient by means of a strap or corresponding means.

Further, The inlet channel 13 branches out from a supply channel 20. Usually two systems of channels 11, 12 and 13 are situated next to each other in the plastic body, and channels 11 can each be attached to a nostril, especially in the case of newborn infants. With tests using an attachment for newborn infants, the channels had the following inner diameters. Channel 11 had a diameter of 3.5 mm, channel 12 had a diameter of 4.0 mm and channel 13 had a diameter of 1.3 mm. Body 19 is consequently relatively small and light so that it can rest comfortably against the patient's face. Channels 11 and 12 are relatively short in length, preferably five times their diameter at the most.

One example is wherein the plastic body 19A has two parallel systems of channels 11, 12 and 13 as in FIG. 2. Channel 20 has a connection tube 21 for attachment of a hose for fresh-gas supply. Channels 11 have two connection tubes 22 to which the attachment 23 in FIG. 3 can be attached.

The examples are intended only to illustrate the invention and are not intended to limit the scope of the invention which is defined by the claims. Some examples of the invention are shown in the attached drawings.

The invention claimed is:

1. A nebulizing device for use in a system for generating a continuous positive airway pressure (CPAP) for newborn infants for simultaneously adding a nebulized drug, comprising:

a branch-channel which at one end thereof is adaptable to fit with a branch-channel of a CPAP device and which at the other end thereof is adaptable to fit with a tube of an attachment device, said attachment device being applicable at the newborn infant, wherein the nebulizing device comprises a nebulizing channel provided for introducing the nebulized drug, generated by a remote nebulizer outputting the nebulized drug at a nebulizer flow, wherein the nebulizing channel is positioned at the branch-channel of the nebulizing device so that the nebulizing channel and a portion of the branch-channel between the nebulizing channel and said other end defines an angle $\alpha \geq 120°$;

wherein the nebulizing channel is dimensioned so that a flow speed in the nebulizing channel is essentially lower than a flow speed at an inlet channel of the CPAP device;

wherein during inspiration/inhalation a volume of the nebulized drug introduced by the nebulizing channel is at least equal to an inspired/inhaled volume by the newborn infant;

wherein said branch-channel of the nebulizing device is arranged to ventilate expiration from the newborn infant through said branch-channel of the nebulizing device in a direction from said other end to said one end and past an inlet opening of the nebulizing channel;

wherein the nebulizing flow in the nebulizing channel is 5-12 I/min;

wherein the branch-channel of the nebulizing device has an inner diameter of 2-5 mm;

wherein the inlet-channel has an inner diameter of 0.5-2.0 mm;

wherein the nebulizing channel has an inner diameter <5 mm.

2. A nebulizing device according to claim 1, wherein the nebulizing device is connected to a CPAP device.

3. A nebulizing device according to claim 1, wherein the nebulizing device is connected to a nebulizing attachment device.

4. A nebulizing device according to claim 1, wherein the inlet-channel has an inner diameter of 1-1.3mm.

5. A method of treatment for Idiopathic Respiratory Distress syndrome IRDS, Respiratory Distress syndrome RDS, Pneumonia, or Obstructive airway disease using a device according to any one of the preceding claims by delivering a nebulised drug to an infant.

6. A nebulizing device for use in a system for generating a continuous positive airway pressure (CPAP) for newborn infants for simultaneously adding a nebulized drug, comprising:

a branch-channel, the branch-channel having a first end, which opens into the atmosphere, and a second end, which is adaptable to fit with an attachment being applicable at the newborn infant;

an inlet channel connected with a respective branch-channel of said branch-channel, between said first and second ends of the branch-channel, for introducing fresh gas at a flow which is adjustable to obtain an adjustable positive pressure within the branch-channel; and a nebulizing channel connected with a respective branch-channel of said branch-channel, between said first and second ends of the branch-channel, and closer to the second end than the inlet channel, for introducing the nebulized drug, generated by a remote nebulizer outputting the nebulized drug at a nebulizer flow;

wherein said nebulizing channel is positioned at the branch-channel so that the nebulizing channel and a portion of the branch-channel between the nebulizing channel and said second end define an angle $\alpha \geq 120°$;

wherein said nebulizing channel is dimensioned so that a flow speed in the nebulizing channel is essentially lower than a flow speed at the inlet channel; and wherein said branch-channel is arranged to ventilate expiration from the newborn infant through the branch-channel of the nebulizing device in a direction from said second end to said first end and past an inlet opening of the nebulizing channel;

wherein the nebulizing flow in the nebulizing channel is 5-12 I/min;

wherein the branch-channel of the nebulizing device has an inner diameter of 2-5 mm;

wherein the inlet-channel has an inner diameter of 0.5-2.0 mm;

wherein the nebulizing channel has an inner diameter <5 mm.

\* \* \* \* \*